United States Patent
Fuchigami et al.

(10) Patent No.: US 8,411,925 B2
(45) Date of Patent: Apr. 2, 2013

(54) X-RAY DIAGNOSIS APPARATUS AND IMAGE PROCESSING APPARATUS

(75) Inventors: Ko Fuchigami, Otawara (JP); Satoru Ohishi, Otawara (JP); Yoshiyasu Hayashi, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 676 days.

(21) Appl. No.: 12/700,195

(22) Filed: Feb. 4, 2010

(65) Prior Publication Data
US 2010/0195893 A1  Aug. 5, 2010

(30) Foreign Application Priority Data

Feb. 4, 2009  (JP) ................................ 2009-024055
Jan. 8, 2010  (JP) ................................ 2010-003302

(51) Int. Cl.
*G06K 9/00* (2006.01)
(52) U.S. Cl. ................ 382/131; 382/133; 378/4; 378/5; 378/8; 378/16; 378/19; 702/40; 600/481
(58) Field of Classification Search .................. 382/133; 378/4, 5, 8, 16, 19; 702/40; 600/481
See application file for complete search history.

(56) References Cited

U.S. PATENT DOCUMENTS 7,636,414 B2 *  12/2009  Imaizumi et al. ................. 378/4
2008/0240336 A1 *  10/2008  Miyazaki et al. ................. 378/4
2009/0005693 A1 *  1/2009  Brauner et al. ............... 600/481

FOREIGN PATENT DOCUMENTS

| JP | 10-11604 | 1/1998 |
| JP | 2006-296707 | 11/2006 |
| JP | 2008-61763 | 3/2008 |
| JP | 2009160221 A * | 7/2009 |

OTHER PUBLICATIONS

Google patents search, Nov. 30, 2012.*

* cited by examiner

*Primary Examiner* — Dilek B Cobanoglu
(74) *Attorney, Agent, or Firm* — Oblon, Spivak, McClelland, Maier & Neustadt, L.L.P.

(57) ABSTRACT

A first generating unit generates a plurality of blood vessel image data sets at the plurality of imaging angles by performing subtraction processing for the plurality of mask image data sets and the plurality of contrast image data sets. A second generating unit generates a blood vessel volume data set including an artery region, a vein region, and a capillary vessel region by performing reconstruction processing for the plurality of blood vessel image data sets. A third generating unit generates a capillary vessel volume data set associated with the capillary vessel region by removing the artery region and the vein region from the blood vessel volume data set. A fourth generating unit generates a capillary vessel image data set by performing three-dimensional image processing for the capillary vessel volume data set.

18 Claims, 9 Drawing Sheets

X-RAY DIAGNOSIS APPARATUS AND IMAGE PROCESSING APPARATUS

CROSS-REFERENCE TO RELATED APPLICATIONS

This application is based upon and claims the benefit of priority from prior Japanese Patent Applications No. 2009-024055, filed Feb. 4, 2009; and No. 2010-003302, filed Jan. 8, 2010, the entire contents of both of which are incorporated herein by reference.

BACKGROUND OF THE INVENTION

1. Field of the Invention

The present invention relates to an X-ray diagnosis apparatus and image processing apparatus which generate image data set concerning perfusion.

2. Description of the Related Art

A capillary vessel image visualizes perfusion in capillary vessels of cerebral blood vessels. In, for example, cerebral blood vessel intervention, a capillary vessel image is very useful to determine whether treatment is complete. In general, an X-ray computed tomography apparatus (X-ray CT apparatus) generates a capillary vessel image data set by using, for example, the technique disclosed in Jpn. Pat. Appln. KOKAI Publication No. 10-11604. More specifically, an X-ray CT apparatus performs threshold processing for volume data set generated by itself using an absolute threshold based on CT values to separate an artery/vein region (a region containing an artery region and a vein region) and a capillary vessel region. Then the apparatus extracts a capillary vessel region. And then the apparatus generates a capillary vessel image data set based on the extracted capillary vessel region. However, in a hospital having no X-ray CT apparatus installed in a manipulation room where intervention is executed, it is necessary to move a patient from the manipulation room to a CT room where an X-ray CT apparatus is installed. This is cumbersome for both the patient and the technician.

If an X-ray diagnosis apparatus (angiography apparatus) can generate capillary vessel image data sets, it is possible to save such cumbersome movement of a patient. The contrast of volume data set generated by an X-ray diagnosis apparatus is unstable as compared with that of volume data set generated by an X-ray CT apparatus because of various reasons (e.g., arterial injection of a contrast medium and a dose). The X-ray diagnosis apparatus cannot therefore perform the same processing as that performed by the X-ray CT apparatus (the separation of an artery/vein region and a capillary vessel region using the absolute threshold based on CT values). For this reason, arteries and veins interfere with the observation of perfusion in cerebral vessels using the X-ray diagnosis apparatus, resulting in a deterioration in observation accuracy.

BRIEF SUMMARY OF THE INVENTION

It is an object of the present invention to provide an X-ray diagnosis apparatus and image processing apparatus which improves the efficiency of catheterization.

According to a first aspect of the present invention, an X-ray diagnosis apparatus includes: an imaging unit configured to comprise an X-ray tube and an X-ray detector to generate a plurality of mask image data sets and a plurality of contrast image data sets at a plurality of imaging angles; a first generating unit configured to generate a plurality of blood vessel image data sets at the plurality of imaging angles by performing subtraction processing for the plurality of mask image data sets and the plurality of contrast image data sets; a second generating unit configured to generate a blood vessel volume data set including an artery region, a vein region, and a capillary vessel region by performing reconstruction processing for the plurality of blood vessel image data sets; a third generating unit configured to generate a capillary vessel volume data set associated with the capillary vessel region by removing the artery region and the vein region from the blood vessel volume data set; and a fourth generating unit configured to generate a capillary vessel image data set by performing three-dimensional image processing for the capillary vessel volume data set.

According to a second aspect of the present invention, an X-ray diagnosis apparatus includes: an imaging unit configured to comprise an X-ray tube and an X-ray detector to generate a plurality of mask image data sets and a plurality of contrast image data sets at a plurality of imaging angles; a first generating unit configured to generate a mask volume data set by performing reconstruction processing for the plurality of mask image data sets; a second generating unit configured to generate a contrast volume data set by performing reconstruction processing for the plurality of contrast image data sets; a third generating unit configured to generate a blood vessel volume data set including an artery region, a vein region, and a capillary vessel region by performing subtraction processing for the contrast volume data set and the mask volume data set; a fourth generating unit configured to generate a capillary vessel volume data set associated with the capillary blood vessel region by removing the artery region and the vein region from the blood vessel volume data set; and a fifth generating unit configured to generate a capillary vessel image data set by performing three-dimensional image processing for the capillary vessel volume data set.

According to a third aspect of the present invention, an X-ray diagnosis apparatus includes: an imaging unit configured to comprise an X-ray tube and an X-ray detector to generate a plurality of mask image data sets and a plurality of contrast image data sets at a plurality of imaging angles; a first generating unit configured to generate a plurality of blood vessel image data sets at the plurality of imaging angles by performing subtraction processing for the plurality of mask image data sets and the plurality of contrast image data sets; a second generating unit configured to generate a blood vessel volume data set by performing reconstruction processing for the plurality of blood vessel image data sets; a segmentation unit configured to segment a blood vessel region included in the blood vessel volume data set into an artery/vein region and a capillary vessel region; and a third generating unit configured to generate a first color image data set or a second color image data set based on the blood vessel volume data set, the first color image data set including the artery/vein region assigned with color information and the capillary vessel region assigned with no color information, the second color image data set including the artery/vein region assigned with no color information and the capillary vessel region assigned with color information.

According to a forth aspect of the present invention, an image processing apparatus includes: a storage unit configured to store a plurality of blood vessel image data sets at a plurality of imaging angles; a first generating unit configured to generate a blood vessel volume data set including an artery region, a vein region, and a capillary vessel region by performing reconstruction processing for the plurality of blood vessel image data sets; a second generating unit configured to generate a capillary vessel volume data set associated with the capillary vessel region by removing the artery region and the vein region from the blood vessel volume data set; and a third generating unit configured to generate a capillary vessel image data set by performing three-dimensional image processing for the capillary vessel volume data set.

According to a fifth aspect of the present invention, an image processing apparatus includes: a storage unit configured to store a plurality of mask image data sets at a plurality of imaging angles and a plurality of contrast image data sets at the plurality of imaging angles; a first generating unit configured to generate a mask volume data set by performing reconstruction processing for the plurality of mask image data sets; a second generating unit configured to generate a contrast volume data set by performing reconstruction processing for the plurality of contrast image data sets; a third generating unit configured to generate a blood vessel volume data set by performing subtraction processing for the contrast volume data set and the mask volume data set, the blood vessel volume data set including an artery region, a vein region, and a capillary vessel region; a fourth generating unit configured to generates capillary vessel volume data set associated with the capillary vessel region by removing the artery region and the vein region from the blood vessel volume data set; and a fifth generating unit configured to generate a capillary vessel image data set by performing three-dimensional image processing for the capillary vessel volume data set.

According to a sixth aspect of the present invention, an image processing apparatus includes: a storage unit configured to store a plurality of mask image data sets and a plurality of contrast image data sets at a plurality of imaging angles; a first generating unit configured to generate a plurality of blood vessel image data sets at the plurality of imaging angles by performing subtraction processing for the plurality of mask image data sets and the plurality of contrast image data sets; a second generating unit configured to generate a blood vessel volume data set by performing reconstruction processing for the plurality of blood vessel image data sets; a segmentation unit configured to segment a blood vessel region included in the blood vessel volume data set into an artery/vein region and a capillary vessel region; and a third generating unit configured to generate a first color image data set or a second color image data set based on the blood vessel volume data set, the first color image data set including the artery/vein region assigned with color information and the capillary vessel region assigned with no color information, and the second color image data set including the artery/vein region assigned with no color information and the capillary vessel region assigned with color information.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An X-ray diagnosis apparatus and image processing apparatus according to each embodiment of the present invention will be described with reference to the views of the accompanying drawing.

First Embodiment

Figure 1:
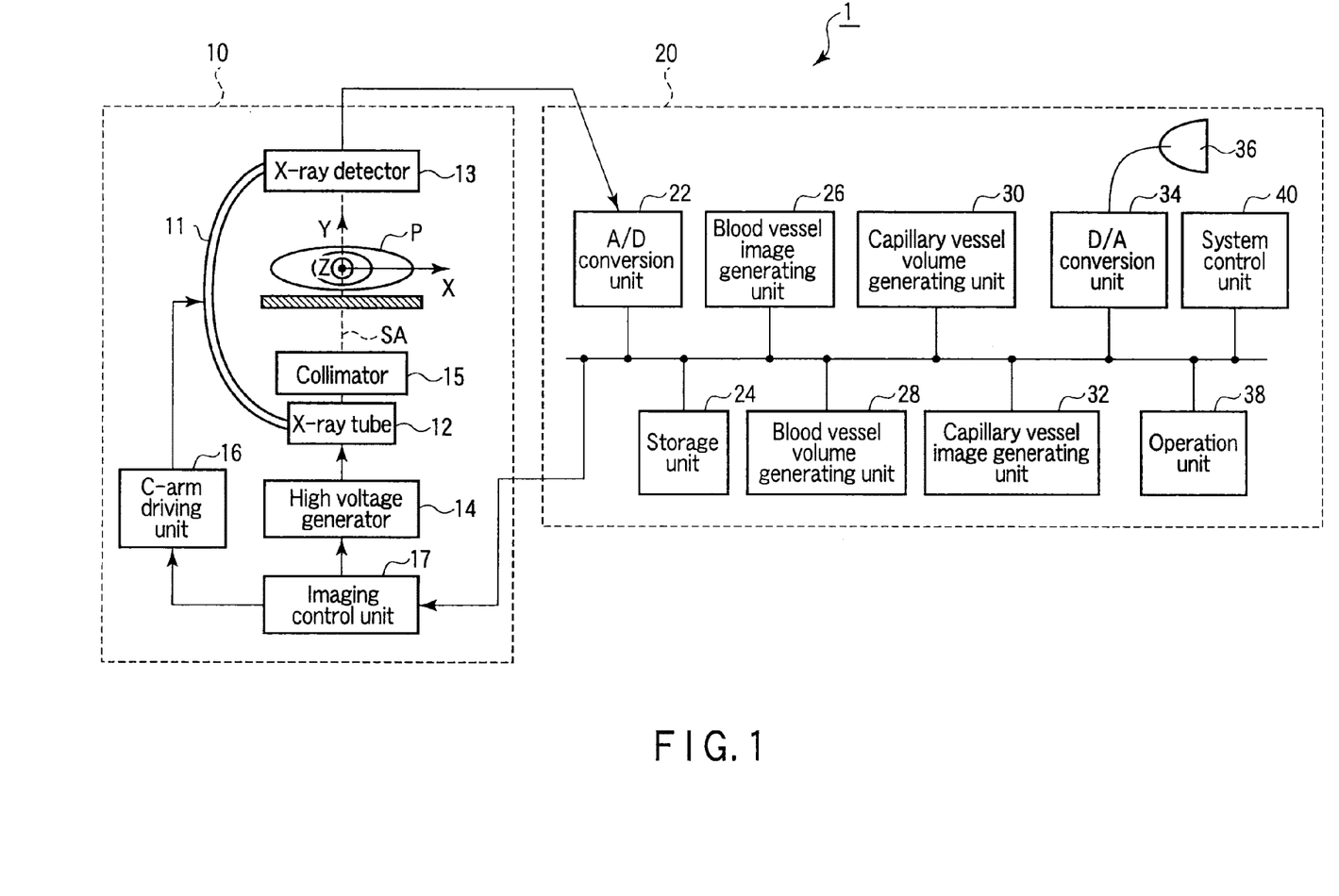
FIG. 1 is a block diagram showing the arrangement of an X-ray diagnosis apparatus according to the first embodiment of the present invention.

FIG. 1 is a block diagram showing the arrangement of an X-ray diagnosis apparatus according to the first embodiment. As shown in FIG. 1, an X-ray diagnosis apparatus 1 includes an imaging unit 10 and an image processing apparatus 20.

As shown in FIG. 1, the imaging unit 10 has a C-arm 11. An X-ray tube 12 and an X-ray detector 13 are mounted on the C-arm 11. The X-ray tube 12 generates X-rays upon reception of a high voltage from a high voltage generator 14. A Collimator 15 is attached to the X-ray tube 12. The Collimator 15 limits the irradiation field of X-rays generated from the X-ray tube 12.

The X-ray detector 13 outputs an image signal by detecting the X-rays generated from the X-ray tube 12 and transmitted through a Subject P. The X-ray detector 13 includes a flat panel detector (FPD) having a plurality of semiconductor detection elements arranged in the form of a matrix. Note that the X-ray detector 13 can include a combination of an image intensifier and a TV camera instead of the FPD.

The C-arm 11 can rotate along the three orthogonal axes, i.e., X-, Y-, and Z-axes, so as to freely change the imaging angle relative to the Subject P. Typically, an imaging angle is defined as the intersection angles of an imaging axis SA relative to the three orthogonal axes, i.e., the X-, Y-, and Z-axes. Conventionally, an imaging angle is defined as angles at the first oblique position (RAO), second oblique position (LAO), third oblique position (LPO), and fourth oblique position (RPO). The imaging axis SA is defined as a straight line extending from the X-ray focus of the X-ray tube 12 and passing through the detection surface center of the X-ray detector 13. Typically, the Z-axis is defined as an axis almost coinciding with the body axis of the object P. The Y-axis coincides with the imaging axis SA. The Z-, Y-, and X-axes intersect at an isocenter (fixed imaging point). The C-arm 11 moves to an imaging angle in accordance with a driving signal from a C-arm driving unit 16.

An imaging control unit 17 controls the high voltage generator 14 and the C-arm driving unit 16 to radiograph an imaging region of the subject P under the control of a system control unit 40 (to be described later). More specifically, the imaging control unit 17 controls the high voltage generator 14 to make the X-ray tube 12 generates a predetermined dose of X-rays. The imaging control unit 17 also controls the C-arm driving unit 16 to position the C-arm 11 at a predetermined imaging angle. The imaging control unit 17 holds an angle table in which a plurality of imaging angles at which radiography is performed are registered. The imaging control unit 17 rotates the C-arm 11 about the Z-axis under the control of the system control unit 40, and causes the X-ray tube 12 to generate X-rays when determining that the C-arm 11 coincides with an imaging angle registered in the angle table. For example, letting N be the number of times of radiography per rotation (360°), an interval $\Delta\theta$ between adjacent imaging angles θn is given by $\Delta\theta=N/360°$. In this case, the imaging angle θn is given by $\Delta n=\theta s+\Delta\theta \times n/360°$ (provided that θs represents an initial angle, and n=0, 1, ..., N−1). The number N of times is, for example, 100 to 200. Note that an imaging region is the head of the subject.

The image processing apparatus 20 includes an A/D conversion unit 22, a storage unit 24, a blood vessel image generating unit 26, a blood vessel volume generating unit 28, a capillary vessel volume generating unit 30, a capillary vessel image generating unit 32, a D/A conversion unit 34, a display unit 36, an operation unit 38, and the system control unit 40.

The A/D conversion unit 22 is connected to the X-ray detector 13. The A/D conversion unit 22 generates X-ray image data by digitizing the image signal output from the X-ray detector 13. Note that an X-ray image associated with a subject P in which no contrast medium is injected and an X-ray image associated with the subject P in which a contrast medium is injected will be respectively referred to as a mask image and a contrast image. Mask images and contrast images are obtained at a plurality of imaging angles θn. The storage unit 24 stores the data of a plurality of mask images and the data of a plurality of contrast images in association with the imaging angles θn.

The blood vessel image generating unit 26 performs subtraction processing for a plurality of contrast image data sets and a plurality of mask image data sets. This subtraction processing generates the plurality of image (to be referred to as blood vessel images hereinafter) data sets associated with the blood vessel contrast-enhanced by a contrast medium. The contrast and mask images subjected to subtraction processing are obtained at the same imaging angles θn. The storage unit 24 stores blood vessel image data sets in association with the imaging angles θn.

The blood vessel volume generating unit 28 generates volume data set associated with a contrast-enhanced blood vessel (to be referred to as blood vessel volume data hereinafter) by performing reconstruction processing for a plurality of blood vessel image data sets. The blood vessel regions contained in blood vessel volume data set include a blood vessel region associated with an artery (to be referred to as an artery region hereinafter), a blood vessel region associated with a vein (to be referred to as a vein region hereinafter), and a blood vessel region associated with a capillary vessel (to be referred to as a capillary vessel region hereinafter). The storage unit 24 stores the blood vessel volume data set.

The capillary vessel volume generating unit 30 generates volume data set associated with only a capillary vessel region (to be referred to as capillary vessel volume data set hereinafter) by removing the artery and vein regions from the blood vessel volume data set. Generation processing of capillary vessel volume data set will be described in detail later. The storage unit 24 stores the capillary vessel volume data set.

The capillary vessel image generating unit 32 generates a two-dimensional image (to be referred to as a capillary vessel image hereinafter) data set associated with the capillary vessel by performing three-dimensional image processing for the capillary vessel volume data set. The storage unit 24 stores the capillary vessel image data set.

The D/A conversion unit 34 is connected to the display unit 36. The D/A conversion unit 34 converts the capillary vessel image data set into analog data set to generate an image signal for driving the display unit 36. The display unit 36 displays the capillary vessel image represented by the image signal generated by the D/A conversion unit 34. As the display unit 36, it is possible to use a display device such as a CRT display, a liquid crystal display, an organic EL display, or a plasma display as needed. Note that when the display device of the display unit 36 is connected to the image processing apparatus 20 via a DVI (Digital Visual Interface) cable or the like, since digital signals can be output without any change, the D/A conversion unit 34 need not be used.

The operation unit 38 accepts various types of commands and information inputs from the operator. As the operation unit 38, it is possible to use a pointing device such as a mouse or a trackball, a selection device such as a mode switch, or an input device such as a keyboard, as needed.

The system control unit 40 functions as the central unit of the X-ray diagnosis apparatus 1, and controls the respective units of the X-ray diagnosis apparatus 1. For example, the system control unit 40 controls the imaging control unit 17 to perform radiography at the plurality of imaging angles θn in response to the imaging start instructions supplied from the operation unit 38. The system control unit 40 also controls the respective units in the image processing apparatus 20 to display a capillary vessel image in response to the request which is supplied from the operation unit 38.

Figure 2:
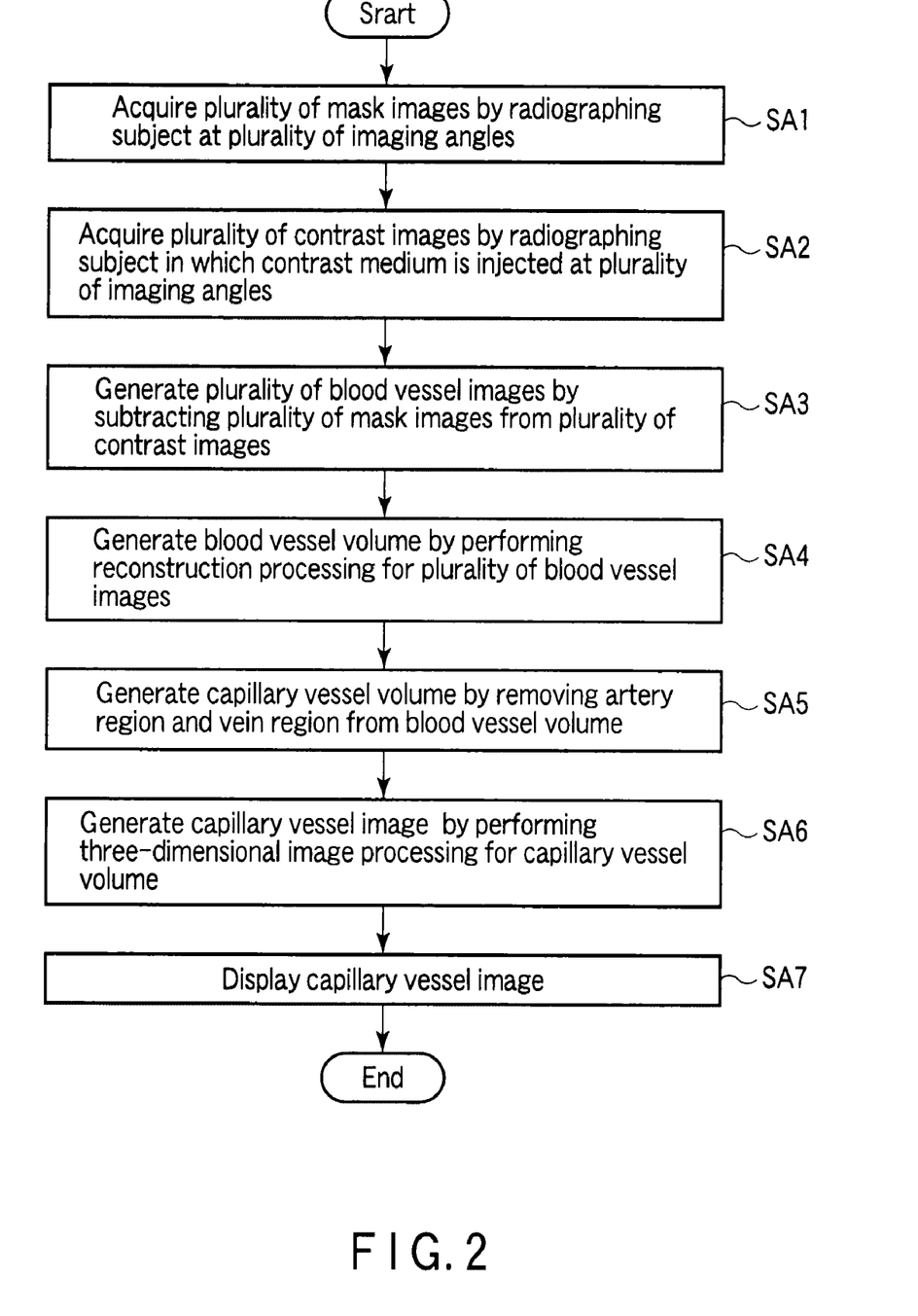
FIG. 2 is a flowchart showing a typical procedure for processing in the first embodiment under the control of a system control unit in FIG. 1.

A procedure for processing in the X-ray diagnosis apparatus 1 according to the first embodiment which is performed under the control of the system control unit 40 will be described next. FIG. 2 is a flowchart showing a typical procedure for this processing.

(Step SA1) When a technician presses the imaging start button via the operation unit 38, the system control unit 40 radiographs the subject P, in which no contrast medium is injected, a plurality of number of times at the plurality of imaging angles θn. With this operation, a plurality of mask image data sets at the plurality of imaging angles θn is acquired. The storage unit 24 stores the mask image data set in association with the imaging angles θn.

(Step SA2) When step SA1 is complete, the technician injects a contrast medium into the subject to enhance the contrast of a cerebral blood vessel in the subject P. When a predetermined period of time has elapsed after the injection of the contrast medium, the system control unit 40 radiographs the subject, in which a contrast medium is injected, a plurality of number of times at the plurality of imaging angles θn. With this operation, a plurality of contrast image data sets at the plurality of imaging angles θn is acquired. The imaging angles θn in step SA1 are equal to the imaging angles θn in step SA2. The storage unit 24 stores the contrast image data set in association with the imaging angles θn.

(Step SA3) When step SA2 is complete, the system control unit 40 causes the blood vessel image generating unit 26 to perform blood vessel image generation processing automatically or in response to a request to display a capillary vessel image which is issued by the technician via the operation unit 38. First of all, the blood vessel image generating unit 26 reads out the mask image data set and the contrast image data set at the same imaging angles θn from the storage unit 24. The blood vessel image generating unit 26 then generates blood vessel image data set by subtracting the mask image data set from the contrast image data set. In this manner, the blood vessel image generating unit 26 generates a plurality of blood vessel image data sets by respectively subtracting the plurality of mask image data sets from the plurality of contrast image data sets. The storage unit 24 stores the generated blood vessel image data set in association with the imaging angles θn.

Note that steps SA2 and SA3 each may be repeated for each imaging angle θn.

(Step SA4) When step SA3 is complete, the system control unit 40 causes the blood vessel volume generating unit 28 to perform blood vessel volume data set generation processing. The blood vessel volume generating unit 28 reads out a plurality of blood vessel image data sets at the plurality of imaging angles θn from the storage unit 24. And the blood vessel volume generating unit 28 performs reconstruction processing for the plurality of blood vessel image data set to generate single blood vessel volume data set. The storage unit 24 stores the blood vessel volume data set.

(Step SA5) When step S4 is complete, the system control unit 40 causes the capillary vessel volume generating unit 30 to perform capillary vessel volume data generation processing. Methods of generating capillary vessel volume data are roughly classified into first method and second method. The first method is a method of generating capillary vessel volume data set by subtracting volume data set associated with artery region and vein region (to be referred to artery/vein volume data set hereinafter) from blood vessel volume data set. The second method is a method of generating capillary vessel volume data set by removing artery region and vein region from blood vessel volume data by performing threshold processing. When artery region and vein region are not specifically discriminated from each other, artery region and vein region will be collectively referred to as an artery/vein region.

Figure 3:
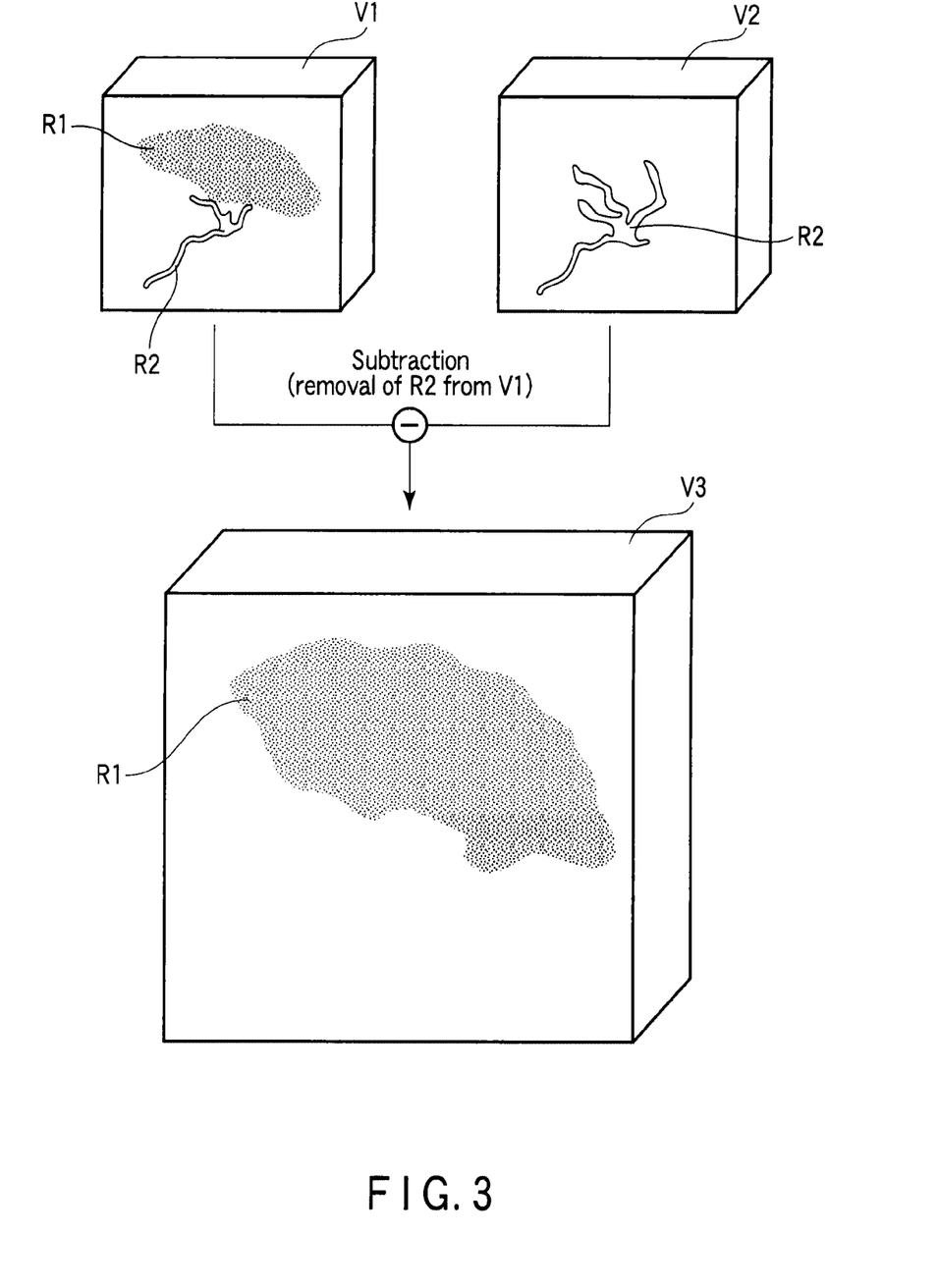
FIG. 3 is a view for explaining step SA5 in FIG. 2.

The first method performed by the capillary vessel volume generating unit 30 (the method of subtracting artery/vein volume data from blood vessel volume data set) will be described first. FIG. 3 is a view for explaining the first method. As shown in FIG. 3, blood vessel volume data set V1 contains all blood vessel regions, i.e., a capillary vessel region R1 and an artery/vein region R2. Although an artery region is not coupled to a vein region in general, they are collectively denoted by one symbol for the sake of descriptive convenience. The capillary vessel region R1 is a set of a plurality of coupled regions. A plurality of coupled regions constituting the capillary vessel region R1 each has a size smaller than that of the artery/vein region R2. Artery/vein volume data set V2 does not contain the capillary vessel region R1 and contains only the artery/vein region R2. Capillary vessel volume data set V3 is therefore generated by subtracting the artery/vein volume data set V2 from the blood vessel volume data set V1.

As methods of generating artery/vein volume data set, it is possible to use various methods. Specific examples of methods of generating artery/vein volume data set will be described below.

First of all, the capillary vessel volume generating unit 30 binarizes a plurality of contrast image data sets at the plurality of imaging angles en, and performs shrinking processing for the plurality of binarized contrast image data sets. In this shrinking processing, when a pixel to be processed (to be referred to as a central pixel hereinafter) has the pixel value "0", all neighboring pixels around the central pixel are replaced by the pixel value "0". The capillary vessel volume generating unit 30 then performs expansion processing for the plurality of image data sets having undergone the shrinking processing. Expansion processing is reverse to shrinking processing. In the expansion processing, when a central pixel has the pixel value "1", all neighboring pixels around the central pixel are replaced by the pixel value "1". Performing the shrinking processing and expansion processing will remove a set of minute coupled regions, i.e., the capillary vessel region, from the contrast image data set. Note that shrinking processing and the expansion processing each may be performed once for each operation. Alternatively, after shrinking processing is performed a plurality of number of times, expansion processing may be performed the same number of times. Note that shrinking processing and expansion processing may be erosion processing and dilation processing, respectively, which are kinds of morphology operations. The capillary vessel volume generating unit 30 then generates artery/vein volume data set by performing reconstruction processing for the plurality of contrast image data sets from which the capillary vessel regions are removed.

The above shrinking/expansion processing needs to binarize data set. An example of shrinking/expansion processing which does not binarize data set will be described next. In shrinking processing, the pixel value of a central pixel is replaced by the average value of the pixel values of the neighboring pixels. In expansion processing, the replaced pixel value (average value) of the central pixel is replaced by the pixel value of a neighboring pixel. With such shrinking/expansion processing which requires no binarization of data set, even if an artery region or vein region having a large size is shrunk/expanded, its pixel value hardly changes. In contrast, if a capillary vessel region having a small size is shrunk/expanded, its pixel value decreases. This will remove the capillary vessel region from the contrast image data set while leaving the artery/vein region.

The second method (the method of performing threshold processing for blood vessel volume data set) performed by the capillary vessel volume generating unit 30 will be described next. This generation processing uses the relative magnitude relationship of voxel value which holds among a voxel value Vc associated with a capillary vessel region, a voxel value Vv associated with a vein region, and a voxel value Va associated with an artery region. In this case, the relative magnitude relationship of voxel value is given by Vc<Vv<Va. That is, threshold processing using a voxel value between the voxel value Vc and the voxel value Vv as a threshold can separate the capillary vessel region and the artery/vein region. The voxels in the blood vessel volume data set which have voxel values equal to or more than this threshold are set to the voxel value "0". This generates capillary vessel volume data set by removing the artery/vein region from the blood vessel volume data set.

Figure 4:
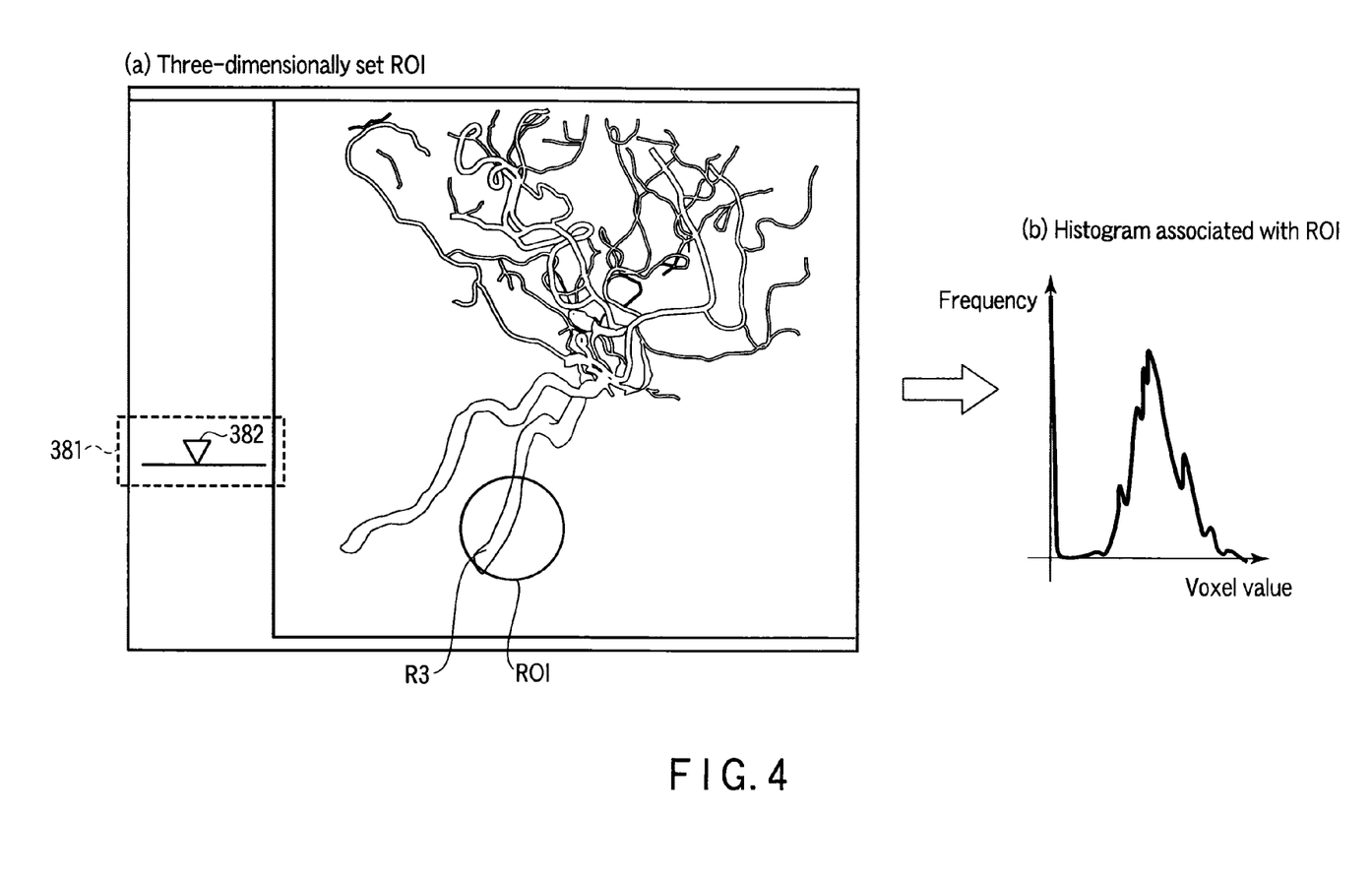
FIG. 4 is another view for explaining step SA5 in FIG. 2.
Figure 5:
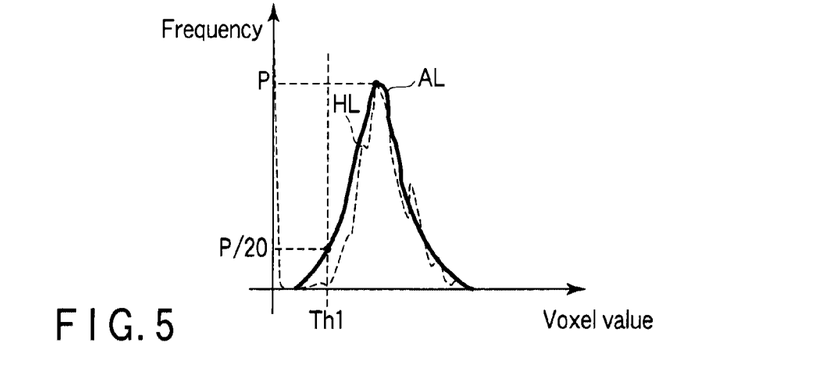
FIG. 5 is still another view for explaining step SA5 in FIG. 2.
Figure 6:
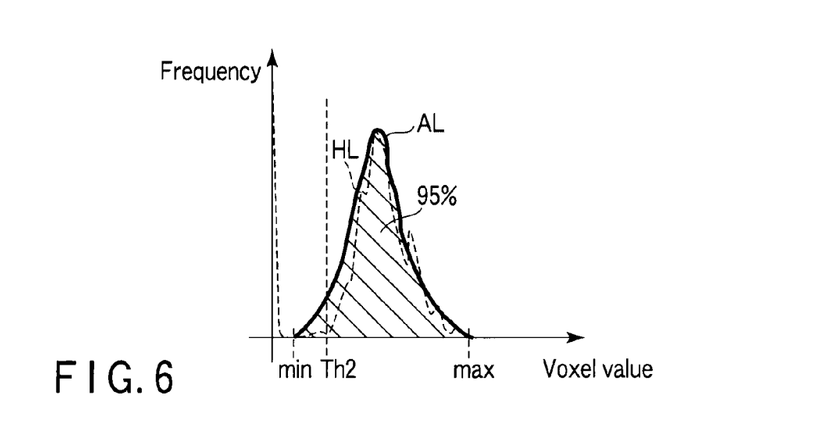
FIG. 6 is still another view for explaining step SA5 in FIG. 2.

There are various methods of setting such a threshold. FIG. 4 is a view showing an example of these threshold setting methods. As shown in FIG. 4, for example, an ROI (Region Of Interest) is three-dimensionally set in the vein region R3 first. This method then calculates a histogram associated with the set ROI. The method specifies voxel values associated with the vein region R3 from the calculated histogram, and sets a predetermined voxel value of the specified voxel values to a threshold. The threshold setting methods include, for example, a method of specifying a threshold from the peak value of the histogram of a vein and a method of calculating a threshold from the area of a histogram. As shown in FIG. 5, the first method is performed according to the following procedure: 1. calculating an approximate curve AL of the histogram of a vein, 2. specifying a maximum value P of the frequency of the approximate curve AL, and 3. setting a voxel value having a frequency of maximum value P/20 to a threshold Th1. As shown in FIG. 6, the second method is performed according to the following procedure: 1. calculating the approximate curve AL of the histogram of the vein, 2. calculating an area S by integrating the entire approximate curve AL, and 3. integrating the approximate curve AL from a maximum voxel value Max to a minimum voxel value Min of the approximate curve AL to calculate integrate value, and setting a voxel value at which the integrate value becomes S×0.95 to a threshold Th2.

The technician may three-dimensionally set an ROI via the operation unit 38. Alternatively, an ROI may be automatically set. When an ROI is to be automatically designated, it is preferable to set a region containing the main part of a vein as an ROI. This is because there are almost no individual differences in the shape and position of the main part (e.g., the internal jugular vein) of a vein. When a region associated with the internal jugular vein is to be set as an ROI, it is preferable to set the lower half of blood vessel volume data set (i.e., the neck side of the subject) as an ROI. The technician may arbitrarily set a threshold via the operation unit 38. In this case, the technician moves a knob 382 of a slider bar 381 via the operation unit 38 shown in FIG. 4 to set, as a threshold, a value corresponding to the position of the knob 382 relative to the slider bar 381.

Figure 7:
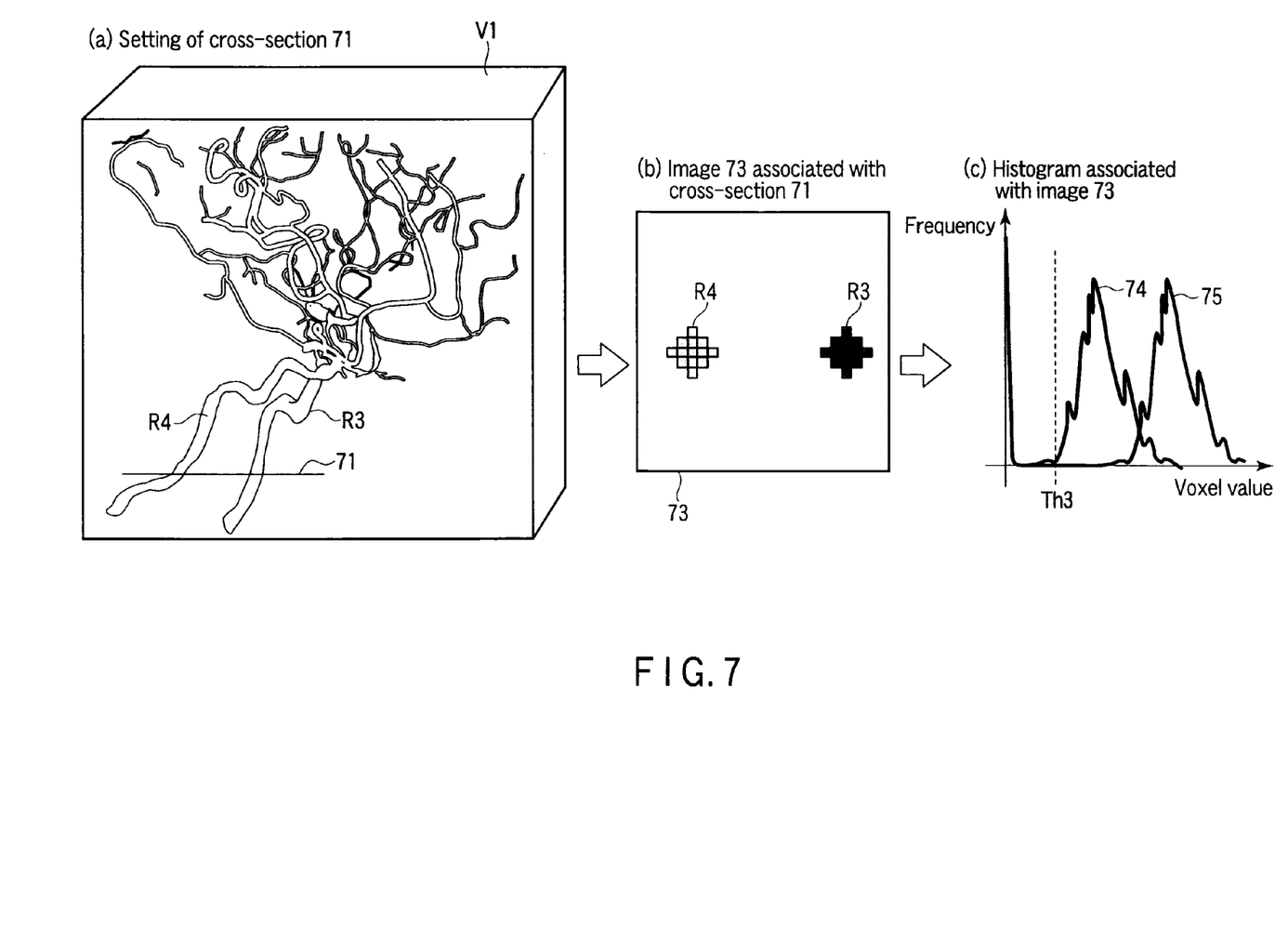
FIG. 7 is still another view for explaining step SA5 in FIG. 2.
Figure 8:
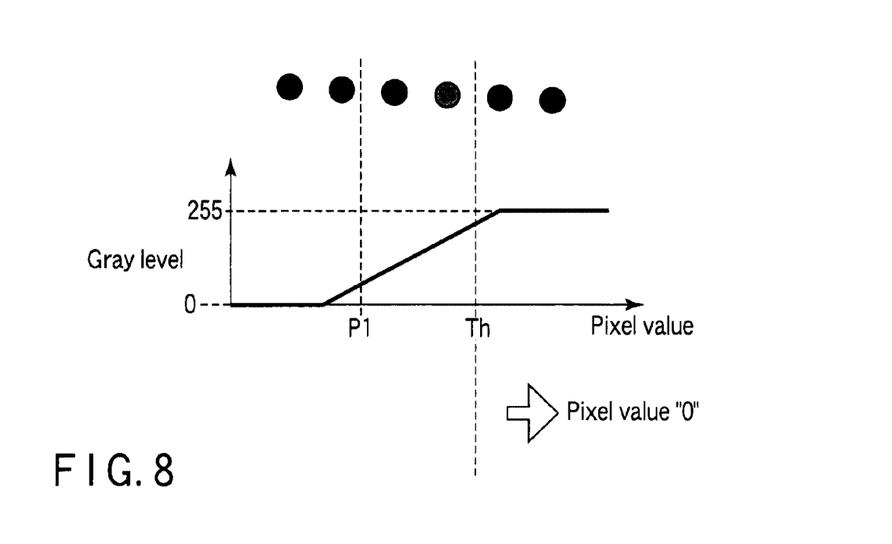
FIG. 8 is a graph for explaining step SA7 in FIG. 2.

As another automatic ROI setting method associated with the second method, the method shown in FIG. 7 is available. As shown in (a) in FIG. 7, first of all, this method automatically sets a cross-section 71 in the blood vessel volume data set V1. The cross-section 71 is, for example, an axial cross-section. The cross-section 71 may also be set at a position on the lower half of the blood vessel volume data set V1, e.g., a position corresponding to ¼ the blood vessel volume data set V1, viewed from below, along the Z-axis. When the cross-section 71 is set, the method generates an image data set 73 associated with the cross-section 71, as shown in (b) in FIG. 7. The image data set 73 contains the vein region R3 and the artery region R4. When the image 73 is generated, the method generates a histogram associated with the image data set 73, as shown in (c) in FIG. 7. The histogram associated with the image data set 73 includes a histogram 74 associated with the vein and a histogram 75 associated with the artery. The histogram 74 associated with the vein shifts more in the direction in which the voxel values decrease than the histogram 75 associated with the artery. Based on the histogram 74 associated with the vein, the method sets a threshold Th3 for the separation of an artery/vein region and a capillary vessel region. The threshold Th3 is set by the above method.

(Step SA6) When step SA5 is complete, the system control unit 40 causes the capillary vessel image generating unit 32 to perform capillary vessel image generation processing. The capillary vessel image generating unit 32 generates capillary vessel image data set by performing three-dimensional image processing for the capillary vessel volume data set. Three-dimensional image processing includes MPR (Multi Planar Reconstruction) processing, volume rendering, surface rendering, and MIP (Maximum Intensity Projection). Note that the technician can arbitrarily set the viewpoint position and line-of-sight direction of a capillary vessel image via the operation unit 38.

(Step SA7) When step SA6 is complete, the system control unit 40 causes the display unit 36 to perform display processing. The display unit 36 displays the capillary vessel image having undergone D/A conversion by the D/A conversion unit 34. When displaying the capillary vessel image by threshold processing, the display unit 36 assigns the minimum gray level "0" to each pixel having a pixel value smaller than a pixel value p1 associated with the capillary vessel. The display unit 36 then assigns the maximum gray level "255" to each pixel having a pixel value equal to or more than a threshold Th4 set in the above manner.

With the above arrangement, the X-ray diagnosis apparatus 1 and image processing apparatus 20 according to the first embodiment can generate capillary vessel volume data set associated with a capillary vessel region by removing vein region and artery region from blood vessel volume data set. For this purpose, the X-ray diagnosis apparatus 1 and the image processing apparatus 20 use relative relationships generally holding between an artery/vein region and a capillary vessel region in X-ray diagnosis apparatuses. The relative relationships include the positional relationship, magnitude relationship of shape, and magnitude relationship of voxel value between an artery/vein region and a capillary vessel region. That is, the X-ray diagnosis apparatus 1 and the image processing apparatus 20 can remove vein region and artery region from blood vessel volume data set with stable accuracy even if the artery/vein region and the capillary vessel region differ in absolute voxel value for each radiography.

The X-ray diagnosis apparatus 1 and the image processing apparatus 20 generate capillary vessel image data set containing only a capillary vessel region based on capillary vessel volume data set. By observing the capillary vessel image, the technician can observe only capillary vessels without being disturbed by arteries or veins. The first embodiment can therefore provide the X-ray diagnosis apparatus 1 and image processing apparatus 20 which allow to observe perfusion in cerebral blood vessels easily and accurately.

Note that in terms of hardware arrangement, the X-ray diagnosis apparatus 1 (image processing apparatus 20) includes a computer for reconstruction processing, i.e., a reconstruction processing unit. The blood vessel volume generating unit 28 generates blood vessel volume data set by performing reconstruction processing for a plurality of blood vessel image data set using this reconstruction processing unit.

Second Embodiment

An image diagnosis apparatus according to the second embodiment of the present invention will be described below. Note that in the following description, the same reference numerals denote constituent elements having almost the same functions as those in the first embodiment, and a repetitive description will be made only when required.

Figure 9:
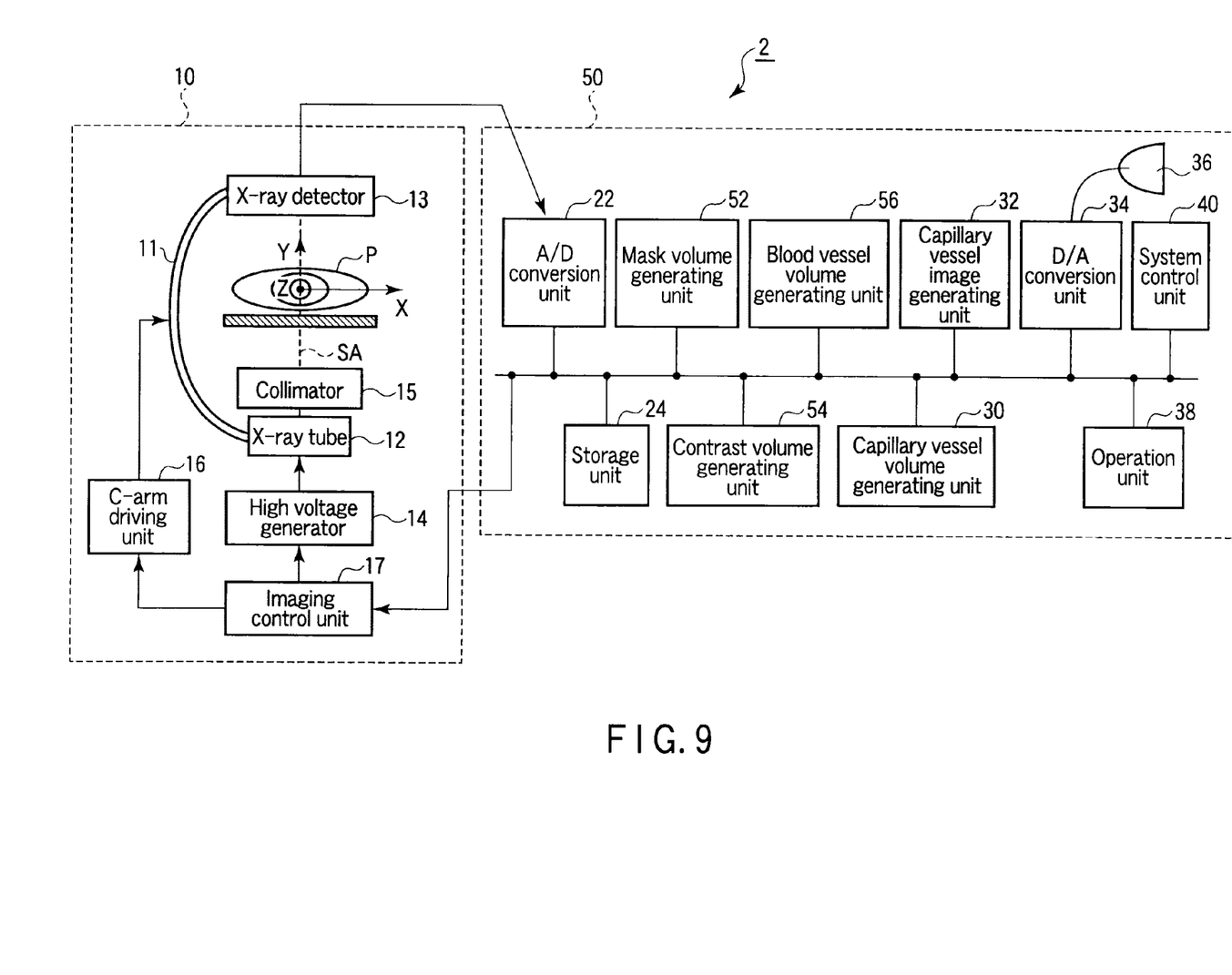
FIG. 9 is a block diagram showing the arrangement of an X-ray diagnosis apparatus according to the second embodiment of the present invention.

FIG. 9 is a block diagram showing the arrangement of an image diagnosis apparatus 2 according to the second embodiment.

As shown in FIG. 9, an image processing apparatus 50 of the image diagnosis apparatus 2 includes an A/D conversion unit 22, a storage unit 24, a mask volume generating unit 52, a contrast volume generating unit 54, a blood vessel volume generating unit 56, a capillary vessel volume generating unit 30, a capillary vessel image generating unit 32, a D/A conversion unit 34, a display unit 36, an operation unit 38, and a system control unit 40.

The mask volume generating unit 52 generates volume data set associated with the subject in which no contrast medium is injected (to be referred to as mask volume data hereinafter) by performing reconstruction processing for a plurality of mask image data set at a plurality of imaging angles θn. The storage unit 24 stores the mask volume data set.

The contrast volume generating unit 54 generates volume data set associated with the subject in which the contrast medium is injected (to be referred to as contrast volume data set hereinafter) by performing reconstruction processing for a plurality of contrast image data set at the plurality of imaging angles θn. The storage unit 24 stores the contrast volume data set.

The blood vessel volume generating unit 56 generates volume data set associated with a blood vessel contrast-enhanced by a contrast medium (to be referred to as blood vessel volume data set hereinafter) by subtracting the mask volume data set from the contrast volume data set. The storage unit 24 stores the blood vessel volume data set.

Figure 10:
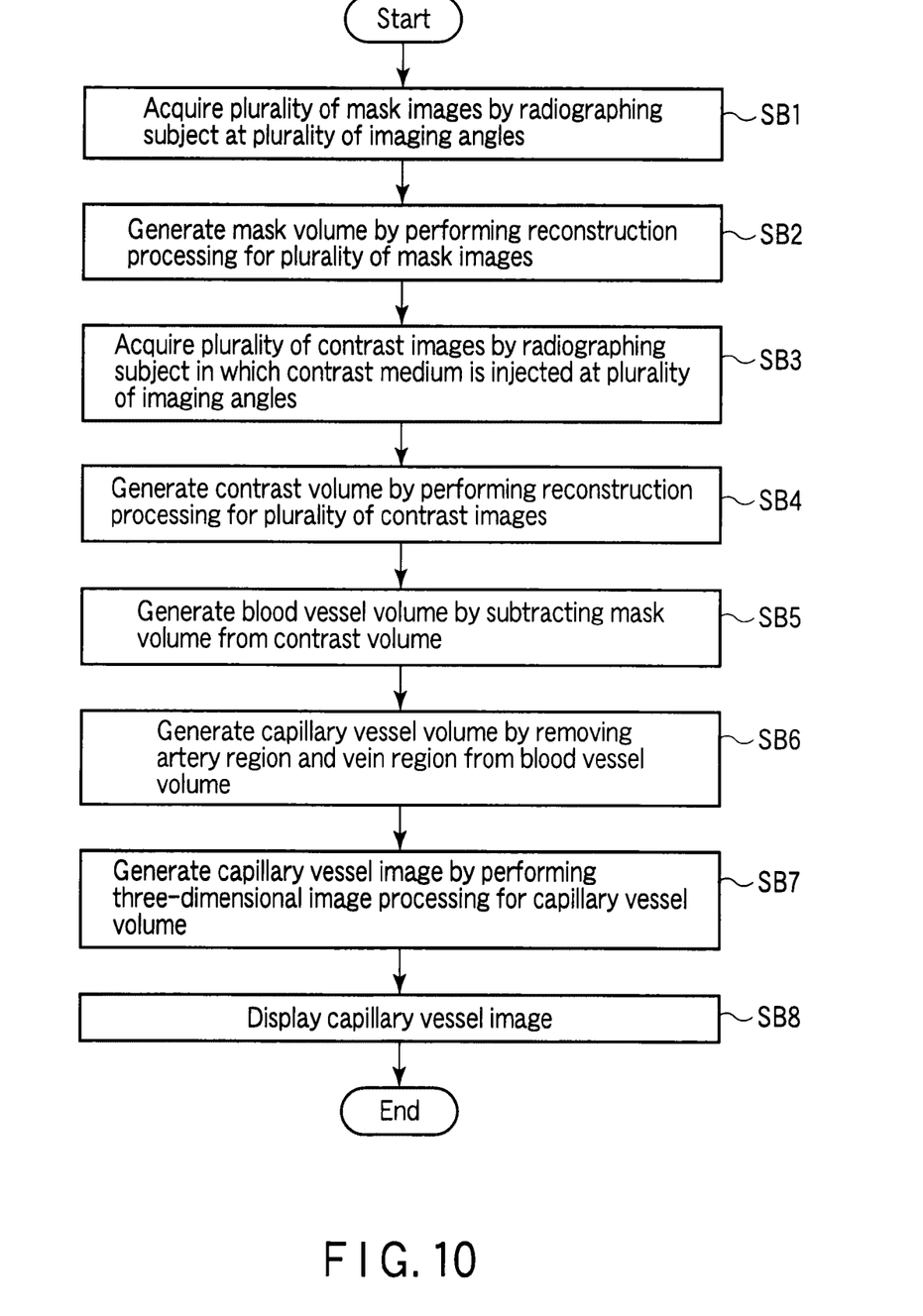
FIG. 10 is a flowchart showing a typical procedure for processing in the second embodiment under the control of a system control unit in FIG. 8.

A procedure for processing in the image diagnosis apparatus 2 according to the second embodiment which is performed under the control of the system control unit 40 will be described next. FIG. 10 is a flowchart showing a typical procedure for this processing.

(Step SB1) When a technician presses the imaging start button via the operation unit 38, the system control unit 40 radiographs a subject P, in which no contrast medium is injected, a plurality of number of times at the plurality of imaging angles θn. With this operation, a plurality of mask image data sets at the plurality of imaging angles θn is acquired. The storage unit 24 stores the mask image data sets in association with the imaging angles θn.

(Step SB2) When step SB1 is complete, the system control unit 40 causes the mask volume generating unit 52 to perform mask volume data set generation processing. The mask volume generating unit 52 reads out a plurality of mask image data sets at the plurality of imaging angles θn from the storage unit 24. And the mask volume generating unit 52 performs reconstruction processing for the plurality of readout mask image data sets to generate mask volume data set. The storage unit 24 stores the generated mask volume data set.

(Step SB3) When step SB2 is complete, the technician injects a contrast medium into the subject P to enhance the contrast of a cerebral blood vessel of the subject P. When the technician presses the imaging start button via the operation unit 38, the system control unit 40 radiographs the subject P, in which the contrast medium is injected, the plurality of number of times at the plurality of imaging angles θn. With this operation, a plurality of contrast image data sets at the plurality of imaging angles θn is acquired. Note that the imaging angles θn in step SB1 are the same as the imaging angles θn in step SB3. The storage unit 24 stores the contrast image data sets in association with the imaging angles θn.

(Step SB4) When step SB3 is complete, the system control unit 40 causes the contrast volume generating unit 54 to generate contrast volume data set in response to a request to display a capillary vessel image which is issued by the technician via the operation unit 38 or automatically. The contrast volume generating unit 54 reads out a plurality of contrast image data sets at the plurality of imaging angles θn from the storage unit 24. And the contrast volume generating unit 54 performs reconstruction processing for the plurality of readout contrast image data sets to generate contrast volume data set. The storage unit 24 stores the generated contrast volume data set.

Note that the order of steps SB1 to SB4 is not limited to the above order. For example, the above steps may be executed in the order of step SB1→step SB3→step SB2→step SB4 or step SB1→step SB3→step SB4→step SB2.

(Step SB5) When step SB4 is complete (in other words, when mask volume data set and contrast volume data set are generated), the system control unit 40 causes the blood vessel volume generating unit 56 to perform blood vessel volume data set generation processing. The blood vessel volume generating unit 56 reads out mask volume data set and contrast volume data set from the storage unit 24. The blood vessel volume generating unit 56 subtracts the readout mask volume data set from the readout contrast volume data set to generate a blood vessel volume data set. The storage unit 24 stores the blood vessel volume data set.

(Step SB6) When step SB5 is complete, the system control unit 40 causes the capillary vessel volume generating unit 30 to perform capillary vessel volume data set generation processing. The capillary vessel volume generating unit 30 generates capillary vessel volume data set by the same method as that in step SA4 in the first embodiment. The storage unit 24 stores the capillary vessel volume data set.

(Step SB7) When step SB6 is complete, the system control unit 40 causes the capillary vessel image generating unit 32 to perform capillary vessel image data set generation processing. The capillary vessel image generating unit 32 generates capillary vessel image data set by the same method as that in step SA6 in the first embodiment. The storage unit 24 stores the capillary vessel image data set.

(Step SB8) When step SB7 is complete, the system control unit 40 causes the display unit to perform display processing. The display unit displays a capillary vessel image by the same method as that in step SA7 in the first embodiment.

With the above arrangement, the image diagnosis apparatus 2 and image processing apparatus 50 according to the second embodiment generate blood vessel volume data set containing a capillary vessel region, a vein region, and an artery region by subtracting the mask volume data set from the contrast volume data set. The image diagnosis apparatus 2 and the image processing apparatus 50 can generate capillary vessel volume data set associated with the capillary vessel region by removing the vein region and artery region from the blood vessel volume data set. As described above, the second embodiment can provide the image diagnosis apparatus 2 and image processing apparatus 50 which allow to observe perfusion in cerebral blood vessels easily and accurately.

Note that in terms of hardware arrangement, the X-ray diagnosis apparatus 2 (image processing apparatus 50) includes a reconstruction processing unit for reconstruction processing. The mask volume generating unit 52 generates a mask volume data set by performing reconstruction processing for a plurality of mask image data sets using this reconstruction processing unit. The contrast volume generating unit 54 also generates a contrast volume data set by performing reconstruction processing for a plurality of contrast image data sets using the reconstruction processing unit.

Modification

A capillary vessel volume generating unit 30 according to a modification specifies the position of a dura matter in mask volume data set, and removes a blood vessel region located closer to the cranial bone side than the position of the dura matter when viewed from a reference point in the blood vessel volume data set (e.g., a central point in the blood vessel volume data set). A vein region may be removed by this method.

Third Embodiment

An image diagnosis apparatus according to the third embodiment of the present invention will be described below. Note that in the following description, the same reference numerals denote constituent elements having almost the same functions as those in the first and second embodiments, and a repetitive description will be made only when required.

Figure 11:
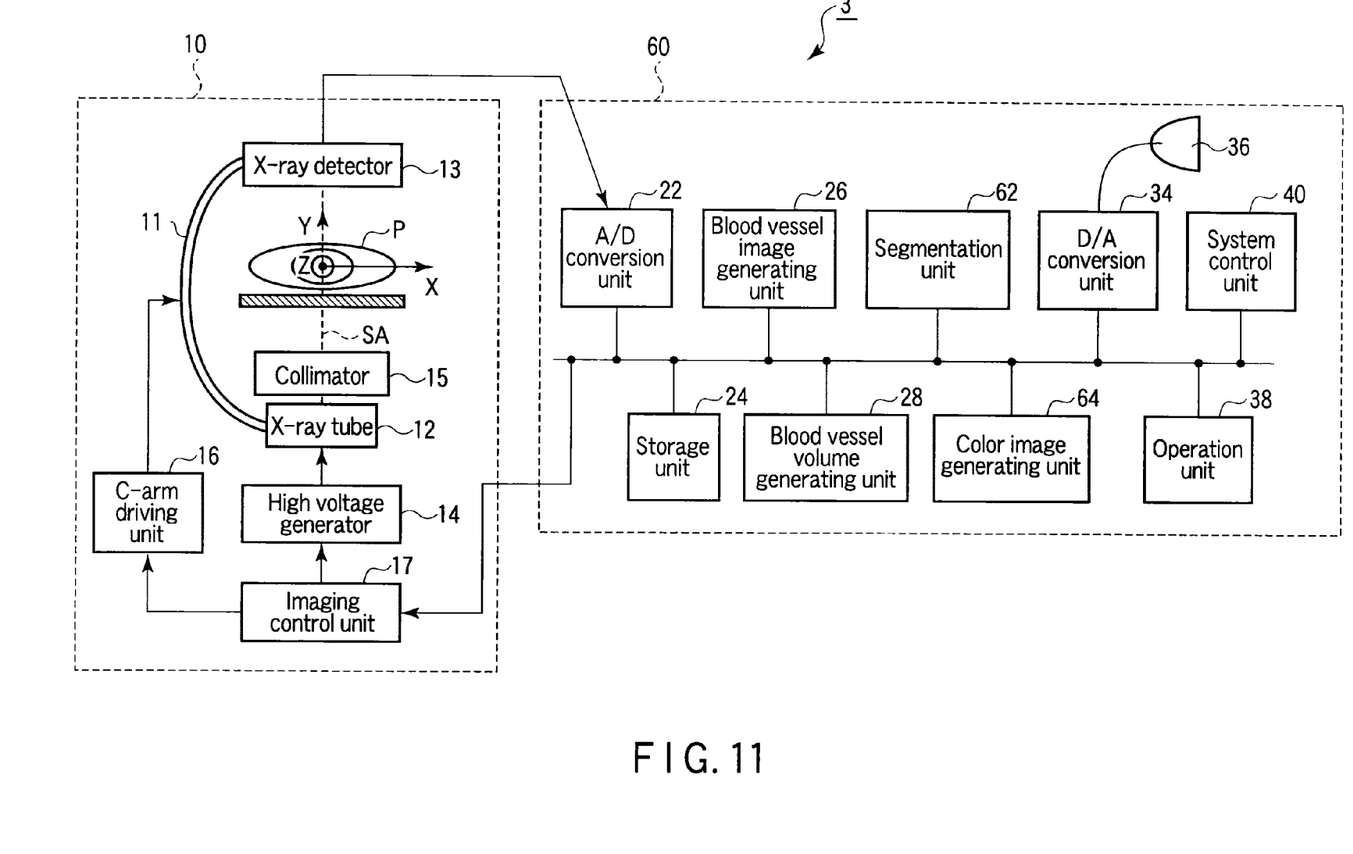
FIG. 11 is a block diagram showing the arrangement of an X-ray diagnosis apparatus according to the third embodiment of the present invention.

FIG. 11 is a block diagram showing the arrangement of an image diagnosis apparatus 3 according to the third embodiment.

As shown in FIG. 11, an image processing apparatus 60 of the image diagnosis apparatus 3 includes an A/D conversion unit 22, a storage unit 24, a blood vessel image generating unit 26, a blood vessel volume generating unit 28, a segmentation unit 62, a color image generating unit 64, a D/A conversion unit 34, a display unit 36, an operation unit 38, and a system control unit 40.

The segmentation unit 62 segments the blood vessel region contained in blood vessel volume data set into an artery/vein region and a capillary vessel region. Segmentation processing includes first segmentation processing and second segmentation processing. The first segmentation processing will be described first. In the first segmentation processing, the segmentation unit 62 generates artery/vein volume data set and capillary vessel volume data set from blood vessel volume data set, thereby segmenting the blood vessel region contained in the blood vessel volume data set into the artery/vein region and the capillary vessel region. The second segmentation processing will be described next. In the second segmentation processing, the segmentation unit 62 performs threshold processing for the blood vessel volume data set to segment the blood vessel region into the artery/vein region and the capillary vessel region. A threshold may be set by using any of the methods described in step SA4. Performing threshold processing based on the threshold set in this manner will segment a blood vessel region into an artery/vein region and a capillary vessel region. In order to identify an artery/vein region and a capillary vessel region, the segmentation unit 62 assigns the first identifier to each voxel associated with the artery/vein region and the second identifier to each voxel associated with the capillary vessel region.

The color image generating unit 64 generates the first color image data set or the second color image data set based on the blood vessel region volume data set.

The first color image is a blood vessel image obtained by assigning color information to the artery/vein region of the blood vessel region and assigning no color information to the capillary vessel region. More specifically, the color image generating unit 64 generates a blood vessel image data set assigned with no color information by performing reconstruction processing for the blood vessel volume data set. In this case, the color image generating unit 64 assigns the first identifier to each pixel originating from each voxel assigned with the first identifier, and assigns the second identifier to each pixel originating from each voxel assigned with the second identifier. Reassigning identifiers will segment the blood vessel region on the blood vessel image data set into an artery/vein region and a capillary vessel region. The color image generating unit 64 then assigns color information to each pixel assigned with the first identifier, and assigns gray level to each pixel assigned with the second identifier. This generates the first color image data set. The gray level set like that in step SA7 is assigned to the capillary vessel region. The artery/vein region in the first image is displayed in color corresponding to the assigned color information. The capillary vessel region in the first color image is displayed in gray corresponding to the assigned gray level.

The second color image is a blood vessel image obtained by assigning no color information to the artery/vein region of the blood vessel region and assigning color information to the capillary vessel region. The second color image data set is also generated by almost the same processing as that for the first color image data set. That is, the color image generating unit 64 assigns gray level to each pixel assigned with the first identifier and assigning color information to each pixel assigned with the second identifier. The artery/vein region in the second color image is displayed in gray corresponding to the assigned gray level. The capillary vessel region in the second color image is displayed in color corresponding to the assigned color information.

Note that it is possible to arbitrarily set a color via the operation unit 38. It is possible to arbitrarily make setting via the operation unit 38 to generate the first color image or the second color image.

With the above arrangement, the image diagnosis apparatus 3 and image processing apparatus 60 according to the third embodiment segment the blood vessel region contained in blood vessel volume data set into an artery/vein region and a capillary vessel region. For this purpose, the image diagnosis apparatus 3 and the image processing apparatus 60 use relative relationships generally holding between an artery/vein region and a capillary vessel region in X-ray diagnosis apparatuses. That is, the X-ray diagnosis apparatus 3 and the image processing apparatus 60 can segment a blood vessel region into an artery/vein region and a capillary vessel region with stable accuracy even if the artery/vein region and the capillary vessel region differ in absolute voxel value for each radiography. The image diagnosis apparatus 3 and the image processing apparatus 60 generate the first color image data set having an artery/vein region displayed in color or the second color image data set having a capillary vessel region displayed in color. By observing the first color image or the second color image, the operator can visually recognize the artery/vein region and the capillary vessel region while visually discriminating them. The third embodiment can therefore provide the image diagnosis apparatus 3 and image processing apparatus 60 which allow to observe perfusion in cerebral blood vessels easily and accurately.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An X-ray diagnosis apparatus comprising:
an imaging unit configured to comprise an X-ray tube and an X-ray detector to generate a plurality of mask image data sets and a plurality of contrast image data sets at a plurality of imaging angles;
a first generating unit configured to generate a plurality of blood vessel image data sets at the plurality of imaging angles by performing subtraction processing for the plurality of mask image data sets and the plurality of contrast image data sets;
a second generating unit configured to generate a blood vessel volume data set including an artery region, a vein region, and a capillary vessel region by performing reconstruction processing for the plurality of blood vessel image data sets;
a third generating unit configured to generate a capillary vessel volume data set associated with the capillary vessel region by removing the artery region and the vein region from the blood vessel volume data set; and a fourth generating unit configured to generate a capillary vessel image data set by performing three-dimensional image processing for the capillary vessel volume data set.

2. The apparatus according to claim 1, further comprising a display unit configured to display the capillary blood vessel image.

3. The apparatus according to claim 1, wherein the third generating unit configured to subtract an artery/vein volume data set associated with the artery region and the vein region from the blood vessel volume data set.

4. The apparatus according to claim 3, wherein the third generating unit configured to generate the artery/vein volume data set by removing the capillary vessel region from the blood vessel volume data set by image processing.

5. The apparatus according to claim 1, wherein the third generating unit configured to set a voxel value between a voxel value of the vein region and a voxel value of the capillary vessel region to a threshold, and performs threshold processing for the blood vessel volume data set based on the threshold to remove the artery region and the vein region from the blood vessel volume data set.

6. An X-ray diagnosis apparatus comprising:
an imaging unit configured to comprise an X-ray tube and an X-ray detector to generate a plurality of mask image data sets and a plurality of contrast image data sets at a plurality of imaging angles;
a first generating unit configured to generate a mask volume data set by performing reconstruction processing for the plurality of mask image data sets;
a second generating unit configured to generate a contrast volume data set by performing reconstruction processing for the plurality of contrast image data sets;
a third generating unit configured to generate a blood vessel volume data set including an artery region, a vein region, and a capillary vessel region by performing subtraction processing for the contrast volume data set and the mask volume data set;
a fourth generating unit configured to generate a capillary vessel volume data set associated with the capillary blood vessel region by removing the artery region and the vein region from the blood vessel volume data set; and
a fifth generating unit configured to generate a capillary vessel image data set by performing three-dimensional image processing for the capillary vessel volume data set.

7. An X-ray diagnosis apparatus comprising:
an imaging unit configured to comprise an X-ray tube and an X-ray detector to generate a plurality of mask image data sets and a plurality of contrast image data sets at a plurality of imaging angles;
a first generating unit configured to generate a plurality of blood vessel image data sets at the plurality of imaging angles by performing subtraction processing for the plurality of mask image data sets and the plurality of contrast image data sets;
a second generating unit configured to generate a blood vessel volume data set by performing reconstruction processing for the plurality of blood vessel image data sets;
a segmentation unit configured to segment a blood vessel region included in the blood vessel volume data set into an artery/vein region and a capillary vessel region; and
a third generating unit configured to generate a first color image data set or a second color image data set based on the blood vessel volume data set, the first color image data set including the artery/vein region assigned with color information and the capillary vessel region assigned with no color information, the second color image data set including the artery/vein region assigned with no color information and the capillary vessel region assigned with color information.

8. The apparatus according to claim 7, wherein the segmentation unit configured to generate a artery/vein volume data set associated with the artery/vein region by removing the capillary vessel region from the blood vessel volume data set to segment the blood vessel region into the artery/vein region and the capillary vessel region, and generate a capillary vessel volume data set associated with the capillary vessel region by removing the artery/vein region from the blood vessel volume data set.

9. The apparatus according to claim 7, wherein the segmentation unit configured to set a voxel value between a voxel value of a vein region of the artery/vein region and a voxel value of the capillary vessel region to a threshold, and segments the blood vessel region into the artery/vein region and the capillary vessel region by performing threshold processing for the blood vessel volume data set based on the threshold.

10. An image processing apparatus comprising:
a storage unit configured to store a plurality of blood vessel image data sets at a plurality of imaging angles;
a first generating unit configured to generate a blood vessel volume data set including an artery region, a vein region, and a capillary vessel region by performing reconstruction processing for the plurality of blood vessel image data sets;
a second generating unit configured to generate a capillary vessel volume data set associated with the capillary vessel region by removing the artery region and the vein region from the blood vessel volume data set; and
a third generating unit configured to generate a capillary vessel image data set by performing three-dimensional image processing for the capillary vessel volume data set.

11. The apparatus according to claim 10, further comprising a display unit configured to display the capillary vessel image.

12. The apparatus according to claim 10, wherein the second generating unit configured to subtract an artery/vein volume data set from the blood vessel volume data set, the artery/vein volume data set including the artery region and the vein region.

13. The apparatus according to claim 12, wherein the second generating unit configured to generate the artery/vein volume data set by removing the capillary vessel region from the blood vessel volume data set by image processing.

14. The apparatus according to claim 10, wherein the second generating unit configured to set a voxel value between a voxel value of the vein region and a voxel value of the capillary vessel region to a threshold, and performs threshold processing for the blood vessel volume data set based on the threshold to remove the artery region and the vein region from the blood vessel volume data set.

15. An image processing apparatus comprising:
a storage unit configured to store a plurality of mask image data sets at a plurality of imaging angles and a plurality of contrast image data sets at the plurality of imaging angles;
a first generating unit configured to generate a mask volume data set by performing reconstruction processing for the plurality of mask image data sets;

a second generating unit configured to generate a contrast volume data set by performing reconstruction processing for the plurality of contrast image data sets;

a third generating unit configured to generate a blood vessel volume data set by performing subtraction processing for the contrast volume data set and the mask volume data set, the blood vessel volume data set including an artery region, a vein region, and a capillary vessel region;

a fourth generating unit configured to generates capillary vessel volume data set associated with the capillary vessel region by removing the artery region and the vein region from the blood vessel volume data set; and a fifth generating unit configured to generate a capillary vessel image data set by performing three-dimensional image processing for the capillary vessel volume data set.

16. An image processing apparatus comprising:

a storage unit configured to store a plurality of mask image data sets and a plurality of contrast image data sets at a plurality of imaging angles;

a first generating unit configured to generate a plurality of blood vessel image data sets at the plurality of imaging angles by performing subtraction processing for the plurality of mask image data sets and the plurality of contrast image data sets;

a second generating unit configured to generate a blood vessel volume data set by performing reconstruction processing for the plurality of blood vessel image data sets;

a segmentation unit configured to segment a blood vessel region included in the blood vessel volume data set into an artery/vein region and a capillary vessel region; and a third generating unit configured to generate a first color image data set or a second color image data set based on the blood vessel volume data set, the first color image data set including the artery/vein region assigned with color information and the capillary vessel region assigned with no color information, and the second color image data set including the artery/vein region assigned with no color information and the capillary vessel region assigned with color information.

17. The apparatus according to claim 16, wherein the segmentation unit configured to generate an artery/vein volume data set associated with the artery/vein region by removing the capillary vessel region from the blood vessel volume data set to segment the blood vessel region into the artery/vein region and the capillary vessel region, and generate a capillary vessel volume data set associated with the capillary vessel region by removing the artery/vein region from the blood vessel volume data set.

18. The apparatus according to claim 16, wherein the segmentation unit configured to set a voxel value between a voxel value of a vein region of the artery/vein region and a voxel value of the capillary vessel region to a threshold, and segments the blood vessel region into the artery/vein region and the capillary vessel region by performing threshold processing for the blood vessel volume data set based on the threshold.

* * * * *